(12) United States Patent
Marcoz et al.

(10) Patent No.: US 12,728,208 B2
(45) Date of Patent: Sep. 8, 2026

(54) AUTO-INJECTOR DEVICE EQUIPPED WITH RECONSTITUTION FUNCTIONALITY FOR MULTIPLE CHAMBER DRUG CARTRIDGE

(71) Applicant: BIOCORP PRODUCTION S.A., Issoire (FR)

(72) Inventors: Alain Marcoz, Montmorin (FR); Majid Hihoud, Villette d'Anthon (FR); Quentin Cohas, Issoire (FR)

( * ) Notice: Subject to any disclaimer, the term of this patent is extended or adjusted under 35 U.S.C. 154(b) by 838 days.

(21) Appl. No.: 17/915,887

(22) PCT Filed: Apr. 1, 2020

(86) PCT No.: PCT/IB2020/000311
§ 371 (c)(1),
(2) Date: Sep. 29, 2022

(87) PCT Pub. No.: WO2021/198719
PCT Pub. Date: Oct. 7, 2021

(65) Prior Publication Data

US 2023/0128850 A1 Apr. 27, 2023

(51) Int. Cl.
*A61M 5/20* (2006.01)
*A61M 5/315* (2006.01)

(52) U.S. Cl.
CPC ...... *A61M 5/2066* (2013.01); *A61M 5/31546* (2013.01); *A61M 5/31583* (2013.01)

(58) Field of Classification Search
CPC .. A61M 2005/2407; A61M 2005/2403; A61M 5/24; A61M 5/20; A61M 5/2066;
(Continued)

(56) References Cited

U.S. PATENT DOCUMENTS 4,573,606 A 3/1986 Lewis et al.
5,915,589 A 6/1999 Lim
(Continued)

FOREIGN PATENT DOCUMENTS

WO 2003099357 12/2003
WO 2010123439 10/2010
(Continued)

OTHER PUBLICATIONS

EPO, International Search Report for PCT/IB2020/000311 mailed Oct. 7, 2020 (3 pages).
(Continued)

*Primary Examiner* — Quynh-Nhu H. Vu
(74) *Attorney, Agent, or Firm* — Deirdre M Kvale; DMK Intellectual Property Law PLLC

(57) ABSTRACT

Handheld motor-driven drug reconstitution and auto-injector device (1) having a proximal drive system (2) comprising an elongated body (3) housing a controllable drive motor (6), and an axially drivable piston rod (7), and a distal drug cartridge holder assembly (11) housing a multiple chamber (30, 31) drug cartridge (25), the cartridge holder assembly (11) being releasably attached to a distal zone (23) of the drive system (2), the drive system (2) and cartridge holder assembly (11) being configured to impart a movement to the drug cartridge holder assembly (11) in which said drug cartridge holder assembly (11) is moved from a first substantially extended distal configuration along the central longitudinal axis, to a second substantially collapsed proximal configuration along the central longitudinal axis, the relative movement of the drug cartridge holder assembly (11) effecting reconstitution of an injectable product from substances contained in each of the chambers (30, 31).

16 Claims, 5 Drawing Sheets

(58) Field of Classification Search
CPC ........ A61M 2005/2451; A61M 5/2448; A61M 2005/31588; A61M 2205/82; A61M 2205/8206; A61M 5/31546; A61M 5/31583
See application file for complete search history.

(56) References Cited

U.S. PATENT DOCUMENTS

| | | | | |
|---|---|---|---|---|
| 6,171,276 | B1 * | 1/2001 | Lippe | A61M 5/20 604/67 |
| 9,005,160 | B2 | 4/2015 | Karlsson et al. | |
| 9,061,103 | B2 * | 6/2015 | Kemp | A61M 5/24 |
| 9,744,310 | B2 * | 8/2017 | Kondoh | A61M 5/31576 |
| 10,765,809 | B2 * | 9/2020 | Bechmann | A61M 5/3204 |
| 2001/0005781 | A1 * | 6/2001 | Bergens | A61M 5/2033 604/156 |
| 2002/0047019 | A1 | 4/2002 | Devers | |
| 2002/0088817 | A1 | 7/2002 | Bell-Greenstreet | |
| 2005/0171476 | A1 * | 8/2005 | Judson | A61M 5/14566 604/131 |
| 2006/0180600 | A1 | 8/2006 | Taylor | |
| 2009/0294323 | A1 | 12/2009 | Luciano | |
| 2010/0030374 | A1 | 2/2010 | Saltsov | |
| 2012/0035538 | A1 * | 2/2012 | Elmen | A61M 5/2459 604/200 |
| 2014/0207058 | A1 * | 7/2014 | Hata | A61M 5/20 604/92 |
| 2014/0277702 | A1 | 9/2014 | Shaw | |
| 2015/0320939 | A1 * | 11/2015 | Beek | A61M 5/326 604/193 |
| 2018/0369481 | A1 * | 12/2018 | Pedersen | A61M 5/2448 |
| 2021/0077723 | A1 * | 3/2021 | Marcoz | A61M 5/31568 |

FOREIGN PATENT DOCUMENTS

| | | |
|---|---|---|
| WO | 2014008393 | 1/2014 |
| WO | 2015044102 | 4/2015 |
| WO | 2018068956 | 4/2018 |
| WO | 2019002534 | 1/2019 |
| WO | WO2019121024 | 6/2019 |

OTHER PUBLICATIONS

EPO, Written Opinion for PCT/IB2020/000311 mailed Oct. 7, 2020 (7 pages).
PCT International Search Report for PCT/IB2022/000046, Aug. 31, 2022 (3 pages).
PCT Written Opinion for PCT/IB2022/000046, Aug. 31, 2022 (5 pages).
PCT International Preliminary Report on Patentability for PCT/IB2022/000046, Jul. 22, 2023 (6 pages).

* cited by examiner

AUTO-INJECTOR DEVICE EQUIPPED WITH RECONSTITUTION FUNCTIONALITY FOR MULTIPLE CHAMBER DRUG CARTRIDGE

BACKGROUND

The present invention relates generally to the field of motorised auto-injector drug delivery devices, in particular motorised pen type drug auto-injectors. Such devices are well known generally in the art, and provide a useful alternative to other drug delivery devices, such as manually operated pen-type injectors, especially where users of manual devices encounter difficulties in preparing and or using the devices to effect injection of an injectable product, such as a drug.

A motorised auto-injector known in the art is described in PCT application published as WO03099357. This document discloses a medication injecting apparatus having a motor-driven drive member that when advanced inserts into a fluid container for forcing fluid therefrom. The drive member includes an internal hollow in which fits at least a portion of the motorized driver assembly when the drive member is retracted to allow a compact apparatus to be provided.

An automatic injector is known from WO2014008393A1 which is adapted to receive a cartridge including a barrel, a needle, a plunger assembly, the auto-injector comprising a housing, a cartridge carrier for receiving a portion of the cartridge, a plunger carrier, at least one transfer instrument coupling the cartridge carrier to the plunger carrier, an elongated drive device enabling movement of the plunger carrier, the plunger carrier and/or the cartridge carrier including an opening for receiving the at least one transfer instrument, a motor and a transmission assembly coupling the motor to the elongated drive device. In the auto-injector device described in this document, the barrel, needle, plunger assembly and drug cartridge is insertable into, and removable from, a housing which completely encapsulates and enclosed the barrel, needle and plunger assembly. The housing is shown as being constituted of two parts, an upper part and a lower part, with a hinge along one side of the housing enabling the upper and lower parts to be movably attached with regard one to the other and thereby allow opening and closure of the housing. The housing is designed with a sufficiently hollowed out portion to allow for introduction, and removal when spent, of the cartridge, needle and plunger assembly. The removable battery powered motor drives a threaded screw which supports a movable carriage that meshes with and is indexed on the threads of the threaded screw and moves forward or backward in correspondence to activation of the motor to move in a forward or reverse direction. The indexed movable carriage engages, upon activation of the motor to drive the threaded screw forwards, the plunger assembly to drive the plunger assembly forward and expel the drug contained in the drug cartridge from the cartridge into the needle and form there into the user of the auto-injector.

A further motorised auto-injector is known from PCT application published as WO2015044102A1. This document illustrates an injection pen used to inject an active ingredient into the body of a patient, the device comprising an electric motor, a cartridge for storing the active ingredient, a piston adapted to slide within the cartridge, a mechanism for pushing the piston within the cartridge driven by the motor during an injection, a display screen and means for controlling the quantity of the active ingredient to be injected. The motor, pushing mechanism and cartridge are all aligned along a common longitudinal axis.

As can be seen from the examples of prior art given above, handheld motor-driven auto-injector devices such as motorised pen injectors are known per se, and can be generally deemed to comprise one or more of the following:

- a drive system comprising a hollow elongated body having a substantially central longitudinal axis along the elongated body, and defining a bore extending along said longitudinal axis located within the hollow elongated body, wherein the elongated hollow body of the drive system additionally houses a user controllable drive motor, and an axially drivable piston rod coupled to the motor and located within the bore; and
- a drug cartridge holder assembly attached to, or forming an integral part of, the drive system, the cartridge holder housing a cartridge with an injectable substance, such as a drug.

The documents illustrated above relate generally to either single chamber drug cartridge, or a single syringe configuration, containing a pre-prepared drug formulation to be injected. Unfortunately, not all drugs or drug combinations can be prepared, and/or formulated, for pre-prepared formulations. Some drugs are relatively unstable, or have a relatively short shelf-life, once diluted, dissolved, or otherwise made up into an injectable product formulation. Some therapeutic treatments furthermore require co-administration of separate or similar drugs, and which are incompatible when stored together in conditions used for the normal storage and distribution of injectable drugs. For this reason, multiple simultaneous or sequential drug injection systems have been developed.

Alternatively, motorised drug injection systems, such as auto-injector pens, have been developed that allow the use of multi-chamber cartridges, in which the injectable drug product is made up, or reconstituted, prior to administration. Such a system is known from PCT application published as WO2019002534A1. This document discloses an auto injector for administering a medicament, the auto injector comprising a housing; a cartridge receiver configured to receive a cartridge comprising a first stopper and a cartridge compartment containing the medicament, the cartridge compartment having a first cartridge sub-compartment containing a first medicament component of the medicament and a second cartridge sub-compartment containing a second medicament component of the medicament; a drive module coupled to move a plunger rod between a retracted plunger rod position and an extended plunger rod position, the plunger rod being configured to move the first stopper; a processing unit coupled to the drive module, wherein the processing unit is configured to control the drive module to move the plunger rod from a first plunger rod position to a mix plunger rod position with a mix plunger rod speed, wherein the mix plunger rod position is selected to position the first stopper in a position wherein the first medicament component is mixed with the second medicament component, and to provide an onset signal after a number of completed inversions of the auto injector has been performed.

One of the problems with multiple-chamber drug cartridges is that they can be problematic to mount correctly and safely to the drive system, as the multi-chamber drug cartridges are often only held by on to the drive system by an extremity, usually the proximal extremity, or else they need to be completely encased in the drive system body in order to maintain sufficient axial stability during driving of the piston rod. The bodies of such motorised systems are already quite long anyway, and thus attaching a multi-chamber drug cartridge to the proximal extremity of the drive system body tends to add significant length to the overall length of the auto-injector. This extra length is often the cause of increased usage difficulties for the average users of such systems, as they then find it hard to manipulate and operate the device easily with one hand, which can lead to reduced patient compliance of the associated treatment regime.

SUMMARY

Accordingly, one object of the present invention is the provision of a reduced-length motor driven auto-injector device that also includes an automatic reconstitution functionality in at least a dual chamber cartridge prior to injection, and in which the auto-injector device is a longitudinally axially configured auto-injector, such as pen-type drug injector.

For the purposes of the present, a longitudinally axially configured auto-injector refers to a motorised auto-injector device in which all of the relative functional components are substantially aligned along a common single lengthwise axis of the device, and in which the piston acts along said common lengthwise, or longitudinal, axis. In this regard, the auto-injectors envisaged by the present invention do not relate to box-type auto-injectors, or auto-injectors that include motor driven pistons which are indirectly driven, for example, by a set of orthogonally positioned or angularly displaced gears, drive mechanisms, or motors, compared to the longitudinal axis of movement along which the piston is driven.

Other objects will become apparent from the following descriptions of various embodiments of the invention.

Accordingly, one object of the invention is a handheld motor-driven drug reconstitution and auto-injector device comprising:

a proximal drive system comprising:

an elongated body having a substantially central longitudinal axis along said elongated body, and a bore extending along said longitudinal axis and within said body, the elongated body housing a controllable drive motor, and an axially drivable piston rod coupled to said motor located within said bore; and a distal drug cartridge holder assembly:

configured to house within said assembly a multiple chamber drug cartridge comprising at least a first substance stored in a first chamber, and at least a second substance stored in a respective second chamber, the first and second chambers being located in a nose to tail arrangement in substantial axial alignment with the central longitudinal axis;

wherein the distal drug cartridge holder assembly has a proximal extremity which is releasably attached to a distal zone of the proximal drive system, and a distal extremity configured to receive an injection needle;

the proximal drive system and distal drug cartridge holder assembly being configured to impart a movement to the drug cartridge holder assembly in which said drug cartridge holder assembly is moved from a first substantially extended distal configuration along the central longitudinal axis, to a second substantially collapsed proximal configuration along the central longitudinal axis; and wherein the relative movement of the drug cartridge holder assembly as it is moved along the longitudinal central axis by the drive system, from the first substantially extended distal configuration to the second substantially collapsed proximal configuration effects reconstitution of an injectable product comprising the at least first and second substances located within only one of said at least first or second chambers after said reconstitution.

In the present specification, the terms “proximal” and “distal” are spatial references that are used to define relative spatial position of the various components of the device in relation to normal usage of the auto-injector device when held in the hand of a user. In this regard, “proximal” indicates the position of an object, or a direction of movement or travel of a component of the auto-injector device, that is towards or near the hand of the user holding the device in the manner in which the device is normally handled and operated. In this case, “proximal” means an end of the device grasped by the user that is opposite to another end of the device from which the drug is ejected or injected into the user. Consequently, the “term” distal refers to the position of an object, or a direction of movement or travel of a component of the auto-injector device, that is towards or near the ejection or injection end of the device.

The proximal drive system is therefore located at an end of the auto-injector device that would normally be held, or gripped, in the hand of a user. This is similar to motorised auto-injectors already known in the art, as indicated in the general introduction.

The proximal drive system comprises an elongated body having a substantially central longitudinal axis extending along said elongated body, and a bore extending along said longitudinal axis and within said body. The elongated body and bore can be formed integrally of the same material, or alternatively be formed up of several assembled components, for example, two complementary halves of at least partially hollowed out body material that mate and are held together by suitable attachment means, such as clips or the like, or by welding or adhesive, for example, ultrasonic welding of the complementary halves, one to another. The complementary, at least partially hollowed out body halves together define the longitudinal bore. The elongated body also houses a controllable drive motor, typically located, and housed within the bore of the elongated body and substantially locate at, or adjacent to, a proximal extremity of the drive system elongate body. The drive motor is controllable via a suitably equipped control device, for example, a programmable microcontroller located on a printed circuit board, also either advantageously located on the elongate body of the drive system, or housed within the bore of said elongate body. A user interface, for example an LCD display, can be provided to allow the user to enter commands that will control the auto-injector device and therefore control the drive motor. The user interface can provide access, for example, to a dose setting system comprising dose increase and decrease buttons, dose cancellation and/or reset buttons. At the proximal extremity of the auto-injector device, the bore may be suitably closed by an activation button, which can be connected directly or indirectly, for example, via an electrical or electronic switch component, and via the control device, to the controllable drive motor.

An axially drivable piston rod is coupled to the motor, and is also located within the bore of the elongate body of the drive system. The axially drivable piston rod is connected to the motor, either directly, or via an axle and/or a suitable set of gears, to control the speed and torque applied to the drivable piston rod when the motor is activated. The drivable piston rod is configured to provide axial movement of a piston from a proximal position towards a distal position under the control of a drive motor. Such piston rods are known per se generally for auto-injectors, and usually comprise at list a threaded rod with the threading provided on an outer surface of the road. Advantageously, the drivable piston rod further comprises a piston nut, located around the piston rod, and having an inner threaded surface which engages with outer threaded surface of the piston rod in a complementary manner. When the motor is activated to operate in a forward drive configuration, the piston rod is rotated by the drive motor, and the thread of the piston rod engages with the thread of the piston nut to move the nut along the piston rod in the distal direction. Similarly, if the motor is activated to operate in reverse or rearward drive configuration, the drive motor causes the piston road to rotate in the opposite direction to the forward drive, and thereby cause the piston nut to move in a proximal direction. The nut is provided with a proximal surface that is configured to contact a proximal stopper of a drug cartridge, and thereby push said stopper along inside the drug cartridge. Such general configurations for threaded piston rods, threaded nuts, and stopper engagement of drug cartridges are known per se in the art.

The auto-injector device of the present invention further comprises a distal drug cartridge holder assembly, configured to house within said assembly a multiple chamber drug cartridge comprising at least a first substance stored in a first chamber, and at least a second substance stored in a respective second chamber, the first and second chambers being located in a nose to tail arrangement in substantial axial alignment with the central longitudinal axis.

Drug cartridges in general are also known per se in the art. As mentioned above, for the purposes of the present specification, the drug cartridge comprises at least a first substance stored in a first chamber, and at least a second substance stored in a respective second chamber, the first and second chambers being located in a nose to tail arrangement in substantial axial alignment with the central longitudinal axis. The drug cartridge is therefore preferably a dual-chamber cartridge, of the type known in the art. The first chamber is generally defined as the volume between a first stopper, generally located at a proximal extremity of the drug cartridge, and a second stopper, generally located at a position between the proximal extremity of the drug cartridge and the distal extremity of the drug cartridge. The second chamber is generally defined by the volume between the second stopper and the distal extremity of the drug cartridge, or optionally, a third stopper. The first chamber comprises a first substance, for example, a first component, of an injectable product that requires reconstitution before injection. The second chamber comprises a second substance, for example, generally a different component to the first component, that is necessary for a suitable injectable product to be made up, or reconstituted, before injection. The first substance and/or the second substance can be a powder, a fluid, a liquid, a gel, a gas, and/or any combination thereof. One of the first or second substances can for example be a solute, such as a powder composition. The other of the first or second substances can then be a suitable solvent for that solute, for example a fluid, such as a liquid. For example, the second substance may be a powder composition and the first substance may be a fluid composition, such as are commonly known, for example, water, ethanol, saline solution, buffer solution or a preservative solution. The relative functions and definitions of the first and second substances are only limited to the requirement to constitute together an injectable product when reconstituted, that can act as a drug with suitable pharmaceutical effect. The drug may for example be any number of chemical or biological entities with pharmaceutical activity, for example vaccines, RNA, DNA, proteins, polypeptides, hormones, any manner of pharmaceutically active chemical or biological molecules, or their metabolites, and the like.

Multiple chamber, including dual-chamber, cartridges of the kind envisaged for use in the present invention are generally provided with a bypass that provides fluid communication between the first chamber and the at least second chamber. The cartridge may alternatively have a plurality of bypass sections providing fluid communication between neighbouring chambers. The one or more bypasses are generally closed on initial manufacturing configuration through the positioning of the stoppers separating, and defining the chambers. As these stoppers are moved via distal translational movement of the drive piston and/or nut coming into contact with the first stopper, so each of the stoppers in turn will eventually translate in a distal direction, either through pressure in an upstream chamber being exerted on a downstream stopper, or by direct contact of a previously upstream, or proximally located stopper on a downstream, or distally located stopper, and thereby move the stopper over the bypass to allow fluid communication between one chamber and its next neighbouring chamber, or another suitably connected chamber. The fluid substance in one of the chambers then enters the bypass connected chamber via the bypass, and mixes with the substance in the other chamber to reconstitute the injectable product.

The device according to the invention is further defined in that the distal drug cartridge holder assembly has a proximal extremity which is releasably attached to a distal zone of the proximal drive system, and a distal extremity configured to receive an injection needle. Here again, means for mounting needles onto the distal extremity of cartridge holders in general are well known in the art, for example, via Luer lock systems, outer surface threaded distal tips of the cartridge holder assembly that engage with a corresponding inner thread provided on the cone of a needle holder, and the like. Furthermore, various means of releasably attaching a proximal extremity to a distal zone of the drive system may be envisaged, such as clips, projections and corresponding recesses, for example, bayonet mounts, screw threads provided on an outer surface of a proximal extremity of the cartridge holder assembly, and complementary threading on an inner surface at, or adjacent to, a distal end of the drive system elongated body, and the like. For the purposes of the present specification, a screw threading releasable attachment system is particularly preferred, as these tend to provide both secure, correctly axially aligned, and easily releasable, via unscrewing, attachment of the cartridge holder assembly about the central longitudinal axis of the auto-injector device drive system.

Additionally, the device according to the invention is further defined in that the proximal drive system and distal drug cartridge holder assembly are configured to impart a movement to the drug cartridge holder assembly in which said drug cartridge holder assembly is moved from a first substantially extended distal configuration along the central longitudinal axis, to a second substantially collapsed proximal configuration along the central longitudinal axis. In other words, the cartridge holder assembly is moved relative to the drive system body to effect the collapse, or retraction, of the cartridge holder assembly from an initial extended configuration in a distal position, to a final substantially collapsed position in a proximal position.

The relative movement of the drug cartridge holder assembly as it is moved along the longitudinal central axis by the drive system, from the first substantially extended distal configuration to the second substantially collapsed proximal configuration is responsible for effecting reconstitution of an injectable product comprising the at least first and second substances. By moving the cartridge holder assembly in a proximal direction, the piston rod is brought into contact with the first proximal stopper of the multiple-chamber cartridge, and further collapsing, proximal movement of the cartridge holder assembly, driven by the drive system, continues to push the proximal stopper in a distal direction, which acts on the second intermediate stopper due to the effect of relative pressures in the chambers, pushing the latter in a distal direction to expose the bypass and allow the first substance, for example a fluid such as a solvent, to be forced into the second chamber from the first chamber via the bypass and dissolve the second substance, for example a drug in powdered solute form. When the collapsed configuration of the cartridge holder assembly has been reached, and the injectable product reconstituted, the injectable product is located within only one of the chambers, and in the case of a dual chamber cartridge, located preferably in the second chamber, thereby positioning said injectable product for injection, as would usually be found in a single chamber cartridge comprising a pre-prepared or pre-formulated injectable product.

As has been mentioned above, the cartridge holder assembly engages in relative movement from an extended, distal configuration to a collapsed proximal configuration. A variety of relative movements of the cartridge holder assembly can be envisaged for the present auto-injector and reconstitution device. The cartridge holder assembly is further configured to be operated by the proximal drive system in a reversed relative movement compared to the reconstitution movement, to move the components of the cartridge holder assembly from a proximal, collapsed configuration to a distal, extended configuration, with an aim to allowing removal of the cartridge holder assembly and exchange of the cartridge for a replacement multi-chamber cartridge requiring reconstitution of the substances contained therein.

According therefore to another object of the invention, the relative movement of the drug cartridge holder assembly from the extended configuration to the collapsed configuration includes a telescopic movement. In other words, the cartridge assembly is configured and designed to permit a relative telescopic movement of its components from the extended configuration to the collapsed configuration, under the influence of, and controlled by, the drive system. The telescopic movement of the cartridge holder assembly may be any suitable movement that causes the constitutive components of the cartridge holder assembly to telescope relative to each other when transitioning from the extended configuration to the collapsed configuration.

According therefore to a further object of the invention, the relative movement of the drug cartridge holder assembly from the extended configuration to the collapsed configuration includes both a rotational telescopic movement and a translational telescopic movement. Such combinations of rotational and translational telescopic movements in the cartridge holder assembly have been found to be particularly advantageous. In particular, such combinations allow for a significant reduction in the overall length of the auto-injector and reconstitution device, thereby improving user experience with, and patient acceptance of, the device.

In yet a still further object of the invention, the drug cartridge holder assembly comprises a plurality of interconnected elongated hollow bodies in concentric axial alignment about the longitudinal central axis. The elongated concentrically arranged hollow bodies as envisaged by the present specification are ideally suited to being moved from an extended distal configuration to a collapsed proximal configuration. The number of concentrically arranged hollow bodies for the cartridge holder assembly can potentially be virtually limitless, within the limits of being able to encase and hold a corresponding multiple chamber drug cartridge, but preferably the number of interconnected hollow bodies making up the cartridge holder assembly is preferably between 3 and 5 interconnected elongated hollow bodies, depending on the degree and precision of relative movement that is desired, and the maximum acceptable length that would be useful to a user or patient using the device, and most preferably and advantageously consists of three interconnected elongated hollow bodies, arranged in concentric axial alignment about the longitudinal central axis.

Accordingly, and in line with yet another object of the invention, the drug cartridge holder assembly comprises:

- a first elongated body comprising a bore in axial alignment with the longitudinal axis;
- a second elongated body comprising a bore in axial alignment with the longitudinal axis; and
- a third elongated body comprising a bore in axial alignment with the longitudinal axis,
- the three elongated bodies being interconnected and organised in concentric axial alignment about the longitudinal central axis.

In the above-mentioned arrangement, the first elongated body of the drug cartridge holder assembly and the third elongated body of the drug cartridge holder assembly are advantageously connected respectively to one another via a contact surface comprising an inner surface of the first elongated body, and outer surface of the third elongated body. Such a contact surface can be formed, for example, through corresponding and interacting screw threading provided on each surface. Particularly useful and advantageous functionality has been determined by locating such screw threading on an outer surface of the third elongated body at, or adjacent to, a proximal extremity of the third elongated body of the drug cartridge holder assembly. Similarly, and in a corresponding manner, particularly useful and advantageous functionality has been found by locating the screw threading of the inner surface substantially all the way along an inner, bore-facing surface of the first elongated body of the drug cartridge holder assembly. The consequence of such an arrangement is that, when driven by the drive system, the configured permitted movement of the third elongated body relative to the first elongated body of the drug cartridge holder assembly is a rotational movement about the longitudinal axis and along the contact surface in a proximal direction.

In the above-mentioned arrangement, the second elongated body of the drug cartridge holder assembly is located concentrically around, and extends in a distal direction from a proximal extremity over the first elongated body to a distal extremity. In such an arrangement, the second elongated body of the drug cartridge holder assembly completely covers and surrounds, or substantially covers and surrounds, the whole length of the first elongated body of the cartridge holder assembly.

The first elongated body of the drug cartridge holder assembly and the second elongated body of the drug cartridge holder assembly are connected respectively to one another via a contact surface comprising cooperating interlocking means provided respectively on the second elongated body and on the first elongated body. The respective cooperating interlocking means are configured to allow relative rotational movement of the first elongated body within the bore of the second elongated body. When driven by the drive system, the respective interlocking means cooperate to cause the first elongated body to rotate about the longitudinal axis within the bore of the second elongated body. In this arrangement, the first elongated body of the cartridge holder assembly is mounted coaxially inside, and physically attached to, the second elongated body of the cartridge holder assembly, in order to maintain a suitable coaxial separation from said second elongated body. The physical, rotationally permissible interlocking attachment of the first elongated body of the cartridge holder assembly to the second elongated body of the cartridge holder assembly can be achieved in a variety of ways, for example via radially oriented projections, or a radial annular shoulder, extending outwards from an outer surface of the first elongated body, and located at, or adjacent to a proximal extremity, of the first elongated body. The second elongated body can comprise one or more corresponding recesses to receive and site the projections or shoulder of the first elongated body, or alternatively, a corresponding annular recess or groove, provided at an appropriate proximal location on said second elongated body. In this manner, the first elongated body is not only free to rotate within the second elongated body about the longitudinal axis when driven by the drive system, but will also be rotated within the second elongated body under the impetus of the drive system. Alternatively, the configuration described above can be reversed, with the second elongated body having inwardly directed projections, or an inwardly directly annular shoulder, and a corresponding groove or recess provided on the first elongated body, the result being that the first elongated body is free to rotate about the longitudinal axis when driven by the drive system.

Additionally, the distal extremity of the second elongated body of the drug cartridge holder assembly is located concentrically around, and extends over, at least a proximal extremity of the third elongated body of the drug cartridge holder assembly. The second elongated body is shaped and dimensioned to interact with the third elongate body to prevent distal movement of said third body beyond a predetermined point. Such a configuration can comprise, for example, an annular projection located at the distal extremity of the second elongated body which extends inwardly into the bore of the second elongated body, the annular projection abutting, in the most distal position allowed to the third elongated body, against an outward abutment projection extending from an outer surface of the third elongated body. The abutment projection of the third elongated body is located on the outer surface thereof at a substantially proximal position on the third elongated body. The interaction of the annular inward projection of the second elongated body, and the outward abutment projection of the third elongated body configures and delimits the permitted movement of the third elongated body relative to the second elongated body of the drug cartridge holder assembly and defines said movement as a translational movement along the longitudinal axis in a proximal direction inside the bore of the second elongated body when driven by the drive system.

According to yet another object of the invention, the auto-injector and reconstitution device further comprises a coupling member configured to couple a proximal extremity of the drug cartridge holder assembly to the axially drivable piston rod of the drive system. Accordingly, the coupling member comprises an elongated coupling member body having a bore in axial alignment with the longitudinal axis and housed within the elongated body of the drive system. The coupling member is configured to be free to rotate, about the longitudinal axis, within the bore of the elongated body of the drive system until reconstitution has been completed. Concretely, the coupling member, under the impetus of the activated drivable piston rod, can rotate about the longitudinal axis, until the third elongated body of the cartridge holder assembly has reached its maximum distance of travel in the proximal direction, at which moment the coupling member is prevented from further rotation, as it is locked in rotation about the longitudinal axis against the cartridge holder assembly.

The coupling member and drivable piston rod are connected to each other via corresponding piston drive engagement means provided respectively on the elongated body of the coupling member and the drivable piston rod. Any suitable engagement means are appropriate for such a connection, but typically, and as an example, such respective engagement means can comprise one or more longitudinal slots provided in the coupling member body, running parallel or substantially parallel to the longitudinal axis, and one or more outwardly projecting wings provided on the piston rod, whereby the wings engage in the slots and the slots permit translational movement of the wings, and thereby the piston rod, along the longitudinal axis. Optionally, and advantageously, the projecting wings are automatically biased in a proximal direction after injection, or following removal of the cartridge holder assembly after reconstitution, by a biasing member located in, or on, the coupling member, such as a spring, against which the wings of the drivable piston are brought to bear as they are moved in a distal direction upon driving by the motor in order to effect reconstitution and injection. Once injection has occurred, the cartridge holder assembly is removed, and the uncoupling of the cartridge holder assembly from the coupling member then causes the biasing spring to push back against the wings, driving the piston rod in a proximal direction and bringing it back to its initial position.

The coupling member further comprises distal engagement means configured to engage with a proximal extremity of a first elongate body of the cartridge body holder assembly. When driven by the drive system, the distal engagement means of the coupling member are configured to cause a rotation of the elongate body of the coupling member about the longitudinal axis to be transmitted to the first elongate body of the cartridge holder assembly. Such distal engagement means can be any suitable engagement means such as simple frictional engagement between a distal surface of the coupling member body and, for example, a proximally located inwardly projecting annular shoulder extending from an inner surface of the bore of the first elongated body of the cartridge holder assembly. Preferably, and advantageously, however, the distal engagement means of the coupling member comprise at least one or more splines, or tongues, extending parallel to, and located around, the longitudinal axis, at the distal extremity of the coupling member. These splines or tongues insert into corresponding engagement means, such as grooves, provided at the proximal extremity, for example, on an inside surface, of the first elongated body of the cartridge holder, when the cartridge holder assembly is mounted to the drive system. In the example given, the splines are dimensioned and configured to interact with the grooves to lock together the coupling member and first elongated body of the cartridge holder assembly, so that rotation of one causes rotation of the other to the same degree. It should be understood that the tongues and grooves can be configured in an opposite arrangement, e.g. with the tongues provided on the first elongated body of the cartridge holder assembly and the grooves provided on the coupling member, respectively. In any of these arrangements, rotation of the coupling member caused by driving of the drivable piston by the drive system directly causes the first elongated body of the cartridge assembly holder to rotate in step with the coupling member. This rotation causes the third elongated body to counter-rotate and be drawn into the bore of the first elongated body, until the proximal extremity of the third elongated body abuts against the proximally located annular shoulder provided within the bore of the first elongated body.

As has been mentioned above, the axially drivable piston rod comprises an externally threaded piston rod which is connected to the drive motor. The drivable piston rod further comprises an internally threaded nut, whereby activation of the drive motor drives the threaded rod to engage the internally threaded nut, the interaction of the external thread of the threaded rod, and the internal thread of the threaded nut causing said nut to move along said longitudinal axis from a proximal position to a distal position. The internally threaded nut is provided with piston drive engagement means located on an outer surface of the nut, said piston drive engagement means being configured to engage with respective corresponding engagement means located in, or on, the coupling member. For this purpose, for example, and as indicated above, the threaded nut is advantageously provided with the outwardly projecting wings which interact with the slots provided in the coupling member body. In this way, the threaded nut rod is advanced in a distal direction when the motor is activated and the piston rod driven, the nut translating along the longitudinal axis due to engagement of the wings in the slots, and at the same, stabilising the threaded nut along the longitudinal axis through the interaction between said slots and said wings.

During the reconstitution step, the motor is activated to drive the drivable piston. The respective elongated body of the coupling member, and first elongated body of the cartridge holder assembly, are locked in rotation, for example via the respectively corresponding tongues/spline and grooves as described above. The wings of the threaded nut, which is pushed forward by the threaded drive piston, engage with the slots of the coupling member body, causing the coupling member to rotate and engage with the first elongated body of the cartridge holder assembly, which is also caused to rotate. Rotation of the first elongated body of the cartridge holder assembly causes the third elongated body of the cartridge holder assembly to counter-rotate via the threaded interacting contact surface provided between the first and third elongated bodies of the cartridge holder assembly, thereby retracting the third elongated body into the bore of both the second elongated body and first elongated body of the cartridge holder assembly. This withdrawal, which corresponds to a proximally directed movement of the third elongated body, continues until the proximal extremity of the third elongated body is in abutment with the inwardly projecting annular shoulder of the first elongated body of the cartridge holder assembly. At this point, the first elongated body of the cartridge holder assembly is prevented from rotating further, as it is held between the coupling member and the third elongated body of the cartridge holder assembly. The nut ceases to rotate and is instead pushed in a distal direction by interaction with the threaded piston under the control of the drive motor, until it comes into contact with the first stopper of the multi-chamber cartridge, at which point further driving of the threaded piston and nut pushes the stopper in a distal direction to cause the first and second substances to mix and be reconstituted as has been described above with regard to the general functioning of multi-chamber drug cartridges.

Once reconstitution has been completed, an injection can either follow, for example, by connecting an appropriate needle to the distal extremity of the cartridge holder assembly, and operating the auto-injector in the usual manner to effect injection. After injection, to allow for exchange of the now empty cartridge, the threaded nut can be withdrawn, i.e. moved in a proximal direction by reversing the direction of the drive motor, causing the threaded piston to interact via the respective screw threads with the threaded nut, and cause the nut to moved in a proximal direction once again. This reverse movement will cause the first elongated body of the cartridge holder assembly to rotate in a direction counter to its previous direction of rotation for reconstitution, and thereby cause the third elongated body to be pushed back in the distal direction until the outward projection on the surface thereof comes into abutting contact with the inwardly projecting annular shoulder of the second elongated body of the cartridge holder assembly. As a result, the cartridge holder assembly moves from the collapsed configuration back to the extended configuration before reconstitution was initiated. The cartridge holder assembly can now be uncoupled from the drive system, and a new cartridge inserted into the assembly for a new reconstitution operation and/or injection.

Additionally, if so desired, the drivable piston can be entirely reset at this juncture manually, if so desired, by pressing on the distal extremity of the nut. Such a manual intervention will override the threaded contact engagement between the threaded piston and the nut, and the biasing spring will push against the wings of the nut to force it backwards, in a proximal direction to its initial position.

According to yet a still further embodiment, there is provided a process for the reconstitution of an injectable product contained in a multiple-chamber drug cartridge of an auto-injector device, comprising at least a first substance stored in a first chamber, and at least a second substance stored in a respective second chamber, the first and second chambers being located in a nose to tail arrangement in substantial axial alignment with a central longitudinal axis of the auto-injector device, comprising:

- providing a handheld motor-driven drug reconstitution and auto-injector device as described herein;
- activating a function of said auto-injector device involving at least a reconstitution step prior to injection;
- wherein the reconstitution step comprises driving the drive motor of said device to cause relative movement of the drug cartridge holder assembly along the longitudinal central axis of the device, from a first substantially extended distal configuration to a second substantially collapsed proximal configuration, thereby effecting reconstitution of the injectable product within only one of said at least first or second chambers.

The various objects of the invention, as described above, and other such objects, will become apparent from the following detailed description of an example of a device according to the invention, in conjunction with the enclosed figures, provided for illustrative purposes, and in which

BRIEF DESCRIPTION OF THE DRAWINGS

FIGS. 1 to 5 represent different schematic views of a device according to the invention. FIGS. 4 and 5 differ from FIGS. 2 and 3 mainly in the fact that the cross-section illustrated represents a 90° rotation of the device along a longitudinal axis thereof. Other than that, all elements remain the same as in FIGS. 2 and 3 and are numbered accordingly.

DETAILED DESCRIPTION OF ILLUSTRATIVE EMBODIMENTS

Figure 1:
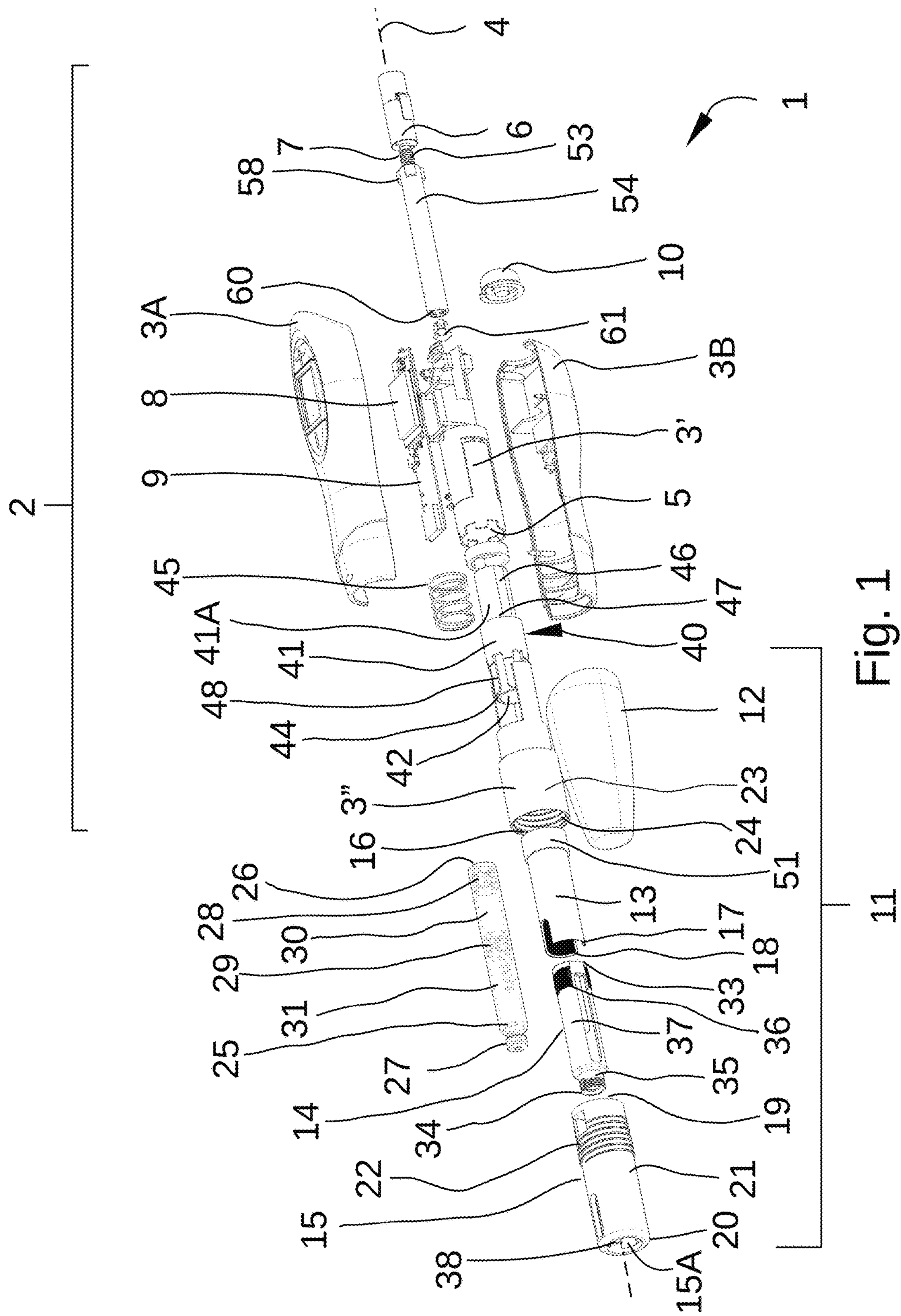
FIG. 1 represents a schematic exploded perspective view of a motor-driven auto-injector and reconstitution device according to the invention.
Figure 2:
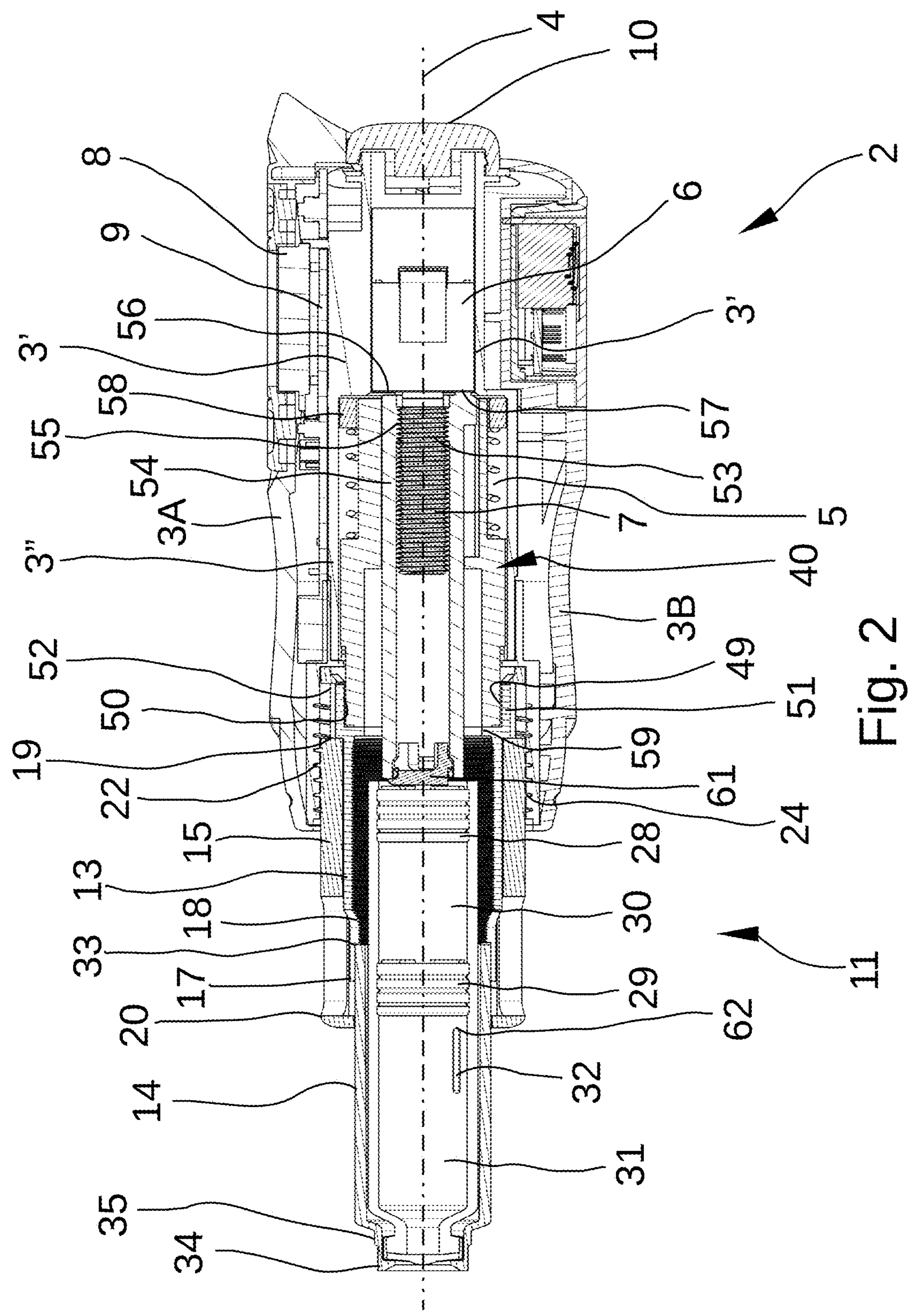
FIG. 2 represents a first schematic cross-section view of the device of FIG. 1, before reconstitution.

Turning now to FIG. 1, a handheld motor-driven drug reconstitution and auto-injector device (1) according to the invention is represented schematically in an exploded perspective view. The device (1) comprises a drive system (2) comprising an elongated body (3', 3") made up of a proximal part (3') and a distal part (3") the proximal and distal parts fitting and interlocking together to form the elongated body (3', 3"), and having a substantially central longitudinal axis (4) along said elongated body (3', 3"). A bore (5) extends along said longitudinal axis (4) and within said body (3', 3"), the elongated body (3', 3") being advantageously enclosed, for example, by two further complementary covers (3A, 3B), which can be fixed together for example by gluing, ultrasonic welding, clipping, of push-fitting together of the two halves (3A, 3B). Preferably, the elongated body (3', 3") is integrally moulded by injection moulding, for example. The elongated body (3', 3") houses a controllable drive motor (6), and an axially drivable piston rod (7) coupled to said motor (6) located within said bore (5). The controllable drive motor is controlled by a controller (8) usefully located on a printed circuit board (9) and appropriately housed within one of the complementary covers (3A, 3B). The controller (8) is a programmable controller such as an EEPROM or other suitable programmable controller, for example a microcontroller, of the type generally known in the art. The controller (8) can integrate, or be connected to, other electrical or electronic components, for example: a power supply such as a battery, optionally rechargeable, or a lithium ion type battery; one or more communications circuits, for example a near-field communications circuit, an RFID circuit, and/or a Bluetooth® communications circuit, such as a Bluetooth® LE circuit for low energy consumption; one or more memory storage components for storing data, including, for example, volatile and/or non-volatile memory storage; one or more sensors connected to the controller for capturing data from the auto-injector device or drive system; one or more display components, configured to display values, or signals, such as visual signals, representing data or functional states of the device, such as an LCD display; one or more user input components configured to enable user input to the device, for example for setting a dose to be administered; and one or more switches for activating or deactivating other components within the device, for example, a proximal button (10) located and seated at the proximal end of the elongated body of the drive system connected to the controller (8) and configured to activate the motor (6) to drive the piston rod (7). The communications circuits are configured, for example, for transmitting information from the auto-injector and reconstitution device (1) to a remote data gathering and processing device, such as a remote or distributed computing system, or for example, a smartphone via a correspondingly programmed application, or to be stored on, or transmitted by, any other kind of mobile telecommunications device, but are also usefully configured to receive information from such remote data gathering and processing devices. As can be seen from FIG. 1, the bore (5) of elongated body (3', 3") houses, along with other components as described herein, the motor (6), and threaded piston rod (7) in axial alignment within the bore (5). The bore (5) is closed by the proximal button (10) which is seated in, and covers, the proximal extremity of the bore (5).

The device (1) further comprises a drug cartridge holder assembly (11). A distal cap (12) is provided to cover the cartridge holder assembly (11) when the latter is mounted to the drive system (2). The cartridge holder assembly comprises three elongated bodies (13, 14, 15) each comprising a bore (13A, 14A, 15A) extending along the longitudinal axis (4). A first elongated body (13), having a proximal extremity (16) and a distal extremity (17) is connected at its proximal extremity (16) to a distal zone of the drive system (2) as will be described herein. The first elongated body (13) has a screw threaded contact surface (18) on an inner surface of the bore (13A) which extends substantially all the way along the bore (13A) from the distal extremity (17) to the proximal extremity (16). A second elongated body (15) having a proximal extremity (19) and a distal extremity (20) has a bore (15A) of greater diameter than either the first elongated body (13) or the third elongated body. In FIG. 1, in the exploded view, the second elongated body (15) is shown distally of both the first and third elongated bodies (13, 14), however, it should be understood that both the first (13) and third (14) elongated bodies are arranged coaxially and concentrically within the bore (15A) of the second elongated body (15) of the cartridge holder assembly (11), and that the second elongated body (15) essentially extends over the whole length of the first elongated body (13). Located adjacent to the proximal extremity (19) of the second elongated body (15), and on the outer surface (21) of the body (15) is a screw thread (22). The screw thread (22) of second elongated body (15) is configured and dimensioned to enable engagement of the second elongated body (15) with a distal area or zone (23) of the distal part of the body (3"), and in particular a screw thread (24) provided on an inner surface of the body (3") facing inwards into the bore (5). Screw thread (24) and screw thread (22) interact and complement each other to form an engagement contact surface that enables the cartridge holder assembly (11) to be removably mounted to the drive system (2), by screwing the cartridge holder assembly into the distal zone of the drive system (2). Additionally, optional corresponding abutment projections are advantageously provided on an inner and/or corresponding outer surface of the elongated bodies (13, 14, 15) in order to facilitate and/or effect longitudinal and axial, and/or respectively superimposed, alignment of optionally provided viewing windows in each of the first and third elongated bodies (13, 14).

Before mounting of the cartridge holder assembly (11) to the distal zone (23) of the drive system (2), and in particular to the distal zone of body (3"), a multiple chamber drug cartridge (25), for example, a dual chamber drug cartridge containing at least a first and second substances to be reconstituted into an injectable product, is inserted axially into the cartridge holder assembly (11) through the bore (13A) of first elongated body (13). The dual chamber drug cartridge (25), for example, made of glass, as shown in FIG. 1 has a proximal extremity (26) and a distal extremity (27), and defines a bore in a known manner in which a first proximal stopper (28) is located at, or substantially adjacent to, the proximal extremity (26) and a second stopper (29) located distally of the first stopper (28) along the bore, thereby forming a first chamber (30). The first chamber (30) comprises a first substance or component of the drug to be reconstituted, for example a solvent. The second stopper (29) furthermore defines a second chamber (31) in the volume that lies distally of the second stopper (29) and between the second stopper (29) and the distal extremity (27) of the cartridge (25). The second chamber (31) contains the second substance or component to be reconstituted, for example a solute powder that is soluble in the solvent, when the components are reconstituted. The first (30) and second chambers (31) are interconnected by a bypass (32), formed as a narrow conduit or passage between the two chambers, and in the initial positions of the stoppers, before reconstitution is operated, the bypass (32) is closed by the second stopper (29), thereby preventing the coming into contact of the first and second substances with each other.

A third elongated body (14) is coaxially and concentrically seated within the bore (13A) of the first elongated body (13). The third elongated body (14) has a proximal extremity (33) and a distal extremity (34). When the drug cartridge is inserted in the holder assembly (11), the distal extremity (27) of the drug cartridge (25) comes to rest, and is engaged, by a neck (35) provided at the distal extremity (34) of the third elongated body (14). The proximal extremity (33) of the third elongated body (14) is provided with a screw threading (36) on an outer surface (37) of the elongated body (14). This screw-threading (36) runs counter directionally to the screw-thread (18) provided on the inner surface of the first elongated body (13), such that when the two screw threads (18, 36) engage each other, for example, through rotation of the first elongated body caused by driving of the motor and threaded piston, the third elongated body is withdrawn into the bore (13A) of the first elongated body (13), moving relative thereto in a proximal direction. At the same time, the third elongated body (14) translates along the bore (15A) of the second elongated body. The second elongated body (15) is provided with an inwardly facing annular shoulder or projection (38), located at its distal extremity (20), which overlaps at least partly with the third elongated body (14) in the initial expanded configuration of the cartridge holder assembly (11). Undesired distal movement of the third elongated body (14) is prevented by engagement of the projecting annular shoulder (38) of the second elongated body (15) with an outwardly projecting abutment (39) provided on the outer surface of the third elongated body.

Figure 4:
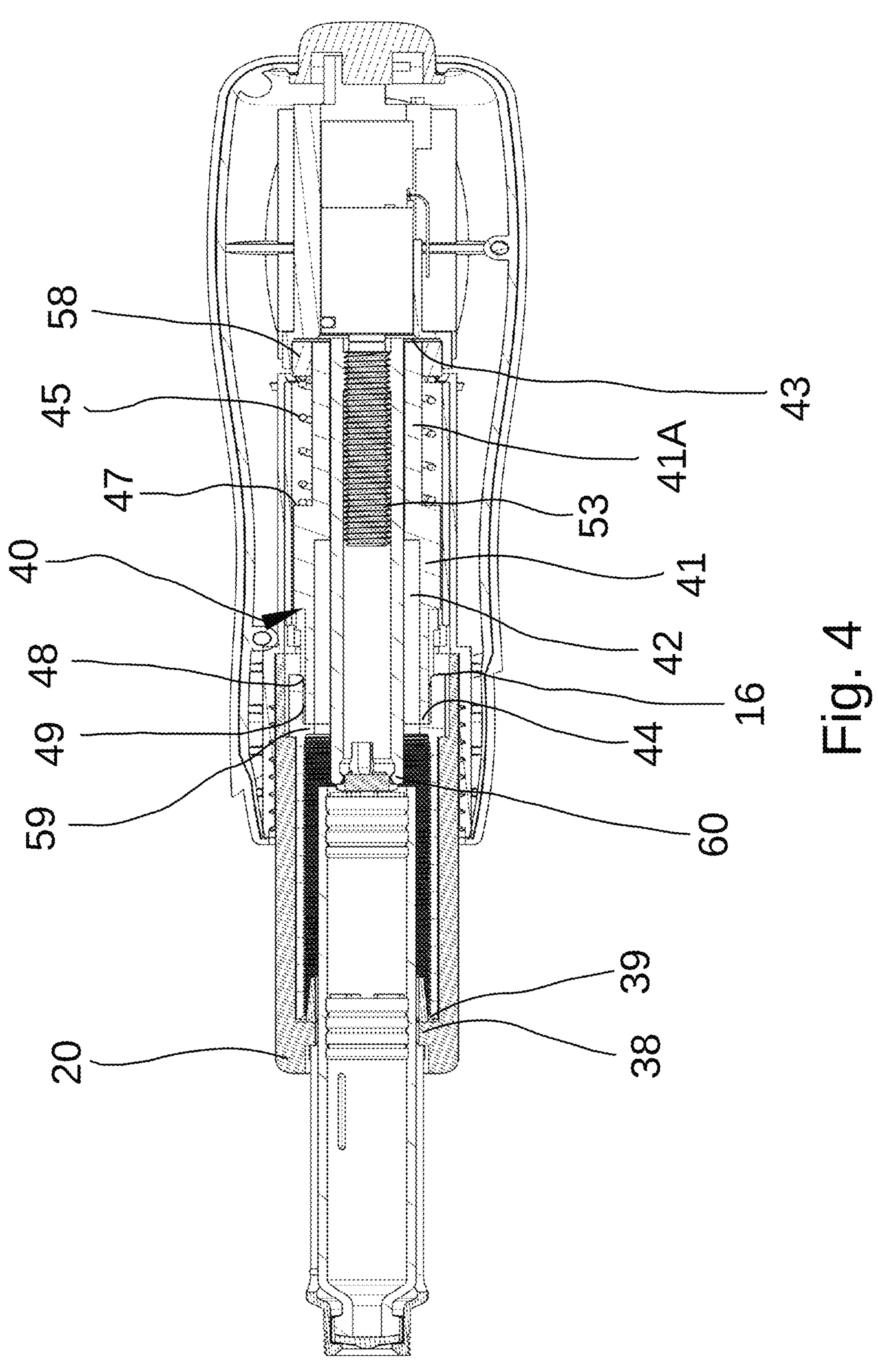
FIG. 4 represents an alternative schematic cross-section view of the device of FIG. 1, before reconstitution.

The auto-injector and reconstitution device (1) further comprises a coupling member (40), configured and dimensioned to rotationally couple the cartridge holder assembly (11) to the drivable drive piston (7). The coupling member comprises an elongated body (41) having a bore (42), a proximal extremity (43) and a distal extremity (44). The elongated body (41) has a portion (41A) of narrower diameter extending from the proximal extremity at least partially along the length of the body (41), for example approximately half way along the length of the body (41). The narrower diameter portion (41A) provides room to accommodate a biasing member (45), such as a coiled spring, located coaxially around an outside surface of said narrowed diameter portion (41A), and seated against a distal extremity of the narrower diameter portion which forms a radially projecting shoulder (47), cf. FIG. 4. The narrower diameter portion (41A) also comprises at least one longitudinal slot (46), and preferably two such slots, preferably diametrically opposed, extending in parallel along the longitudinal axis (4) from the proximal extremity (43) to the distal extremity and shoulder (47) of the portion of narrower diameter (41A). At the distal extremity (44) of the coupling member (40), a plurality of tongues or splines extending in parallel along the longitudinal axis (4), and radially distributed about said axis, are provided. The splines or tongues (48) are configured and dimensioned to engage, and interlock, with correspondingly dimensioned and configured grooves (49), located at the proximal extremity (16) of the first elongated body (13) of the cartridge holder assembly (11), on an inner surface (50) of said body (13) facing inwardly into the bore (13A) thereof. Upon mounting of the cartridge holder assembly to the drive system, such as by screwing the second elongated body (15) into the distal zone (23) of the drive system, the interlocking of the splines or tongues (48) of the coupling member (40) with the grooves (49) of the first elongated body (13) causes the coupling member (40) and the first elongated body (13) to be rotationally locked, meaning that any rotation imparted to the coupling member is transmitted to the first elongated body of the cartridge holder assembly for as long as said body (13) is physically capable of rotating in the direction of rotation applied by the motor via the piston rod (7).

Turning back now to the cartridge holder assembly, the first elongated body (13) is mounted, and held within, the bore (15A) of the second elongated body (15). The first elongated body (13) is provided with interlocking engagement means that interlock with the second elongated body (15) to prevent relative distal or proximal movement between the two bodies (13, 15). Such interlocking means are also configured to allow first elongated body (13) to rotate about the longitudinal axis. An example of suitable interlocking engagement means can be an annular projecting shoulder (51), extending from, or adjacent the proximal extremity (16) of the first elongated body of the cartridge holder assembly, and which engages in a correspondingly dimensioned and configured annular groove (52) provided at, or adjacent to, the proximal extremity (19) of the third elongated body of the cartridge holder assembly. In this way, the first elongated body (13) of the cartridge holder assembly (11) is free to rotate within the bore (15A) and yet prevented from movement in a distal and proximal direction along the longitudinal axis (4).

Figure 3:
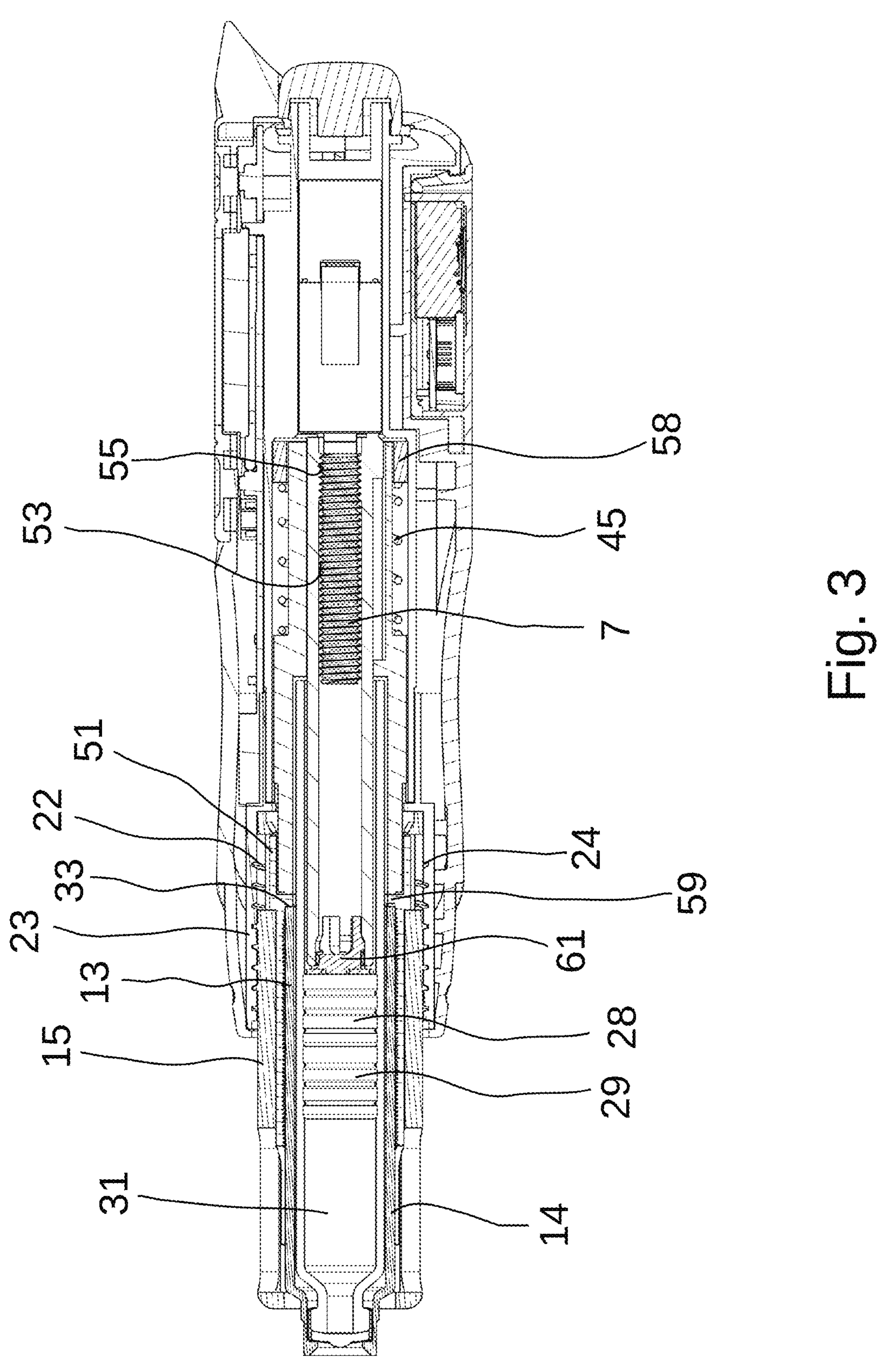
FIG. 3 represents a first schematic cross-section view of the device of FIG. 1, after reconstitution.
Figure 5:
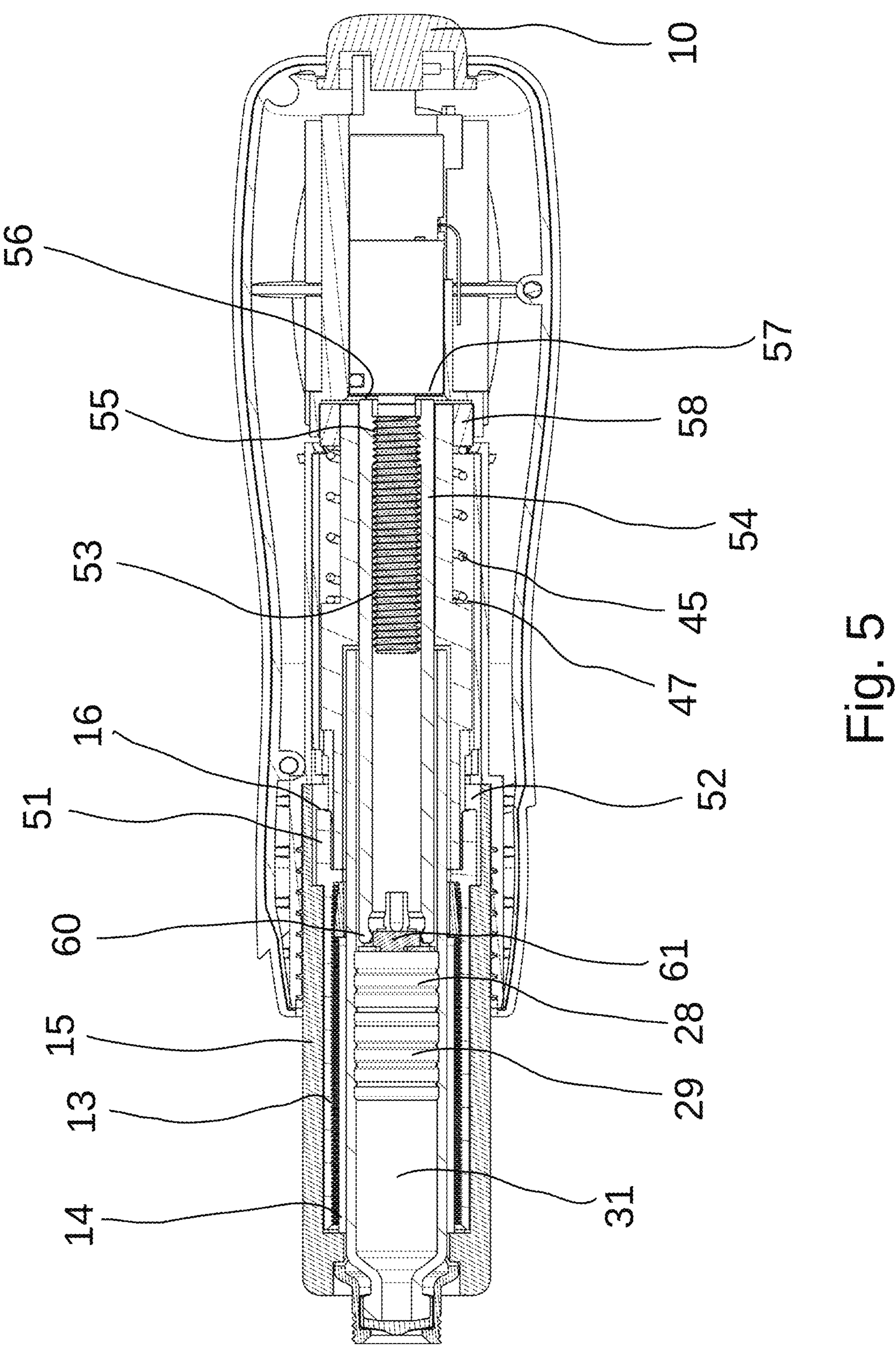
FIG. 5 represents an alternative schematic cross-section view of the device of FIG. 1, after reconstitution.

The threaded piston (7) has a screw thread (53) provided on an outer surface of the piston (7). The piston (7) further comprises a nut (54), provided with an inner threading (55) that runs counter to the threading of the piston (7). The proximal extremity (56) of the nut (54) rests against a distal extremity (57) of the motor (6) in the device (1) before use. Rotating the threaded piston (7) causes the nut (54) to move in a distal direction away from the distal extremity (57) of the motor (6), due to the engagement of the inner threading (55) of the nut (54) with the outer threading (53) of the piston (7). In order to prevent the threaded nut from causing the threaded piston to simply extend to the end of the threading when the motor is activated, for example, by pressing the button switch (10) after having set a dose via the controller (8) to reconstitute and auto-inject, the threaded nut is also provided with a plurality of radially outwardly projecting wings (58), located at the proximal extremity (56) of the nut (54). The wings (58) are configured and dimensioned to engage with the parallel and radially distributed or opposing slots (46) provided on the coupling device. As the nut (54) is constrained rotationally by the interaction of the wings (58) against the slots (46), this results in a rotational force about the longitudinal axis being applied to the coupling member (40). In turn, and because the coupling member (40) is attached to the first elongated body (13) of the cartridge holder assembly (11), this is also brought into rotation. Further rotation of the threaded piston via the drive motor causes the nut (54) to move distally with the wings (58) in the slots (46) against the biasing member (45). Rotation of the coupling member (40), transmitted to the first elongated body (13) of the cartridge holder assembly, causes the internal threading of body (13) to contact the external thread of the third elongated body (14), and thereby withdraw said third body (14) into the bore (13A) of first elongated body (13). This movement in a proximal direction of the third body (14) proceeds until the proximal extremity (33) of the third body (14) comes into abutting contact with an inwardly projecting annular shoulder (59) provided within the bore (13A) of the first body (13) and extending from an inner surface of said body (13) into the bore. Once the third elongated body (14) of the cartridge holder assembly has reached the maximum permitted proximal travel distance, it can no longer rotate. Similarly, body (13) can no longer rotate either, and neither can coupling member (40). The cartridge holder assembly is now fully in the collapsed configuration (cf. FIGS. 3 and 5).

Subsequently, the threaded piston continues to drive the nut (54) in a distal direction, leading to the distal extremity (60) of the nut (54) coming into contact with the first stopper (28). The distal extremity (60) of the nut (54) can advantageously be provided with a cap or insert (61) made out of rubber, elastomer, or a similarly appropriate plastic material, to form a bearing surface of the nut (54) at the distal extremity (60) thereof against the first stopper (28).

Continued activation of the drive motor forces the nut (54) and extremity (60) to advance in a distal direction, pushing the first stopper (28) and the contents of the first chamber (30) in a distal direction. The pressure build up caused by the compression of the contents in the first chamber (30) as the first stopper is moved distally by the nut (54) causes the second stopper (29) to be moved distally as well, until it too has moved beyond a proximal entry (62) of the bypass (32). Once the proximal entry (62) of the bypass (32) has been exposed to the substance in the first chamber, and under continued distal movement of first stopper caused by continued distal movement of the nut (54), the substance in the first chamber, e.g. a solvent liquid, is pushed via the first bypass entry through the bypass (32) into the second chamber, and reconstitution of the two substances is allowed to proceed. The first stopper (28) is continuously pushed via the motor (6), and nut (54) in a distal direction within the drug cartridge until all of the first substance has been forced via the bypass (32) into the second chamber (31) and reconstitution has been effected. An injection needle can now be mounted to the distal extremity (34) of the third elongated body (14) of the cartridge holder assembly, and injection allowed to proceed as per the usual command and control of such auto-injector devices.

Once injection has been completed, and the cartridge now correspondingly empty of any injectable product that was contained therein, the motors direction of rotation can be reversed via the controller and activation button, for example. Reversal of the motors direction causes the nut to move in a proximal direction once more back towards the distal extremity (57) of the motor. In addition, the biasing member (45) pushes against the wings (58) of the nut (54) to facilitate moving the nut (54) backwards in the proximal direction. As movement in the proximal direction progresses, the nut (54) will reach a position where the coupling member (40) and first elongated body (13) of the cartridge holder assembly (11) will once again be free to rotate, under the influence of the wings, this time in an opposite direction to that required for reconstitution, and in doing so, will cause the third elongated body (14) to move in a distal direction once again, taking the cartridge holder assembly (11) from the collapsed state to the extended state. The distal movement of the third elongated body (14) will eventually be halted by the projecting annular shoulder (38) of the second elongated body (15) coming into abutting contact with the outwardly projecting abutment (39) provided on the outer surface of the third elongated body (14). At this point, the nut (54) will have returned to its initial starting position, and the cartridge holder assembly (11) will have reached its initial extended configuration. The cartridge holder assembly (11) can then be removed, and the spent cartridge replaced with a new one to recommence the sequence of reconstitution and injection.

The invention claimed is:

1. A handheld motor-driven drug reconstitution and auto-injector device comprising:

a proximal drive system comprising:

an elongated body having a substantially central longitudinal axis along said elongated body and a bore extending along said longitudinal axis and within said body the elongated body housing a controllable drive motor, and an axially drivable piston rod assembly coupled to said motor located within said bore having a distal tip;

a distal drug cartridge holder assembly having a collapsed configuration and an extended configuration along the central longitudinal axis configured to house a multiple chamber drug cartridge comprising at least a first substance stored in a first chamber, and at least a second substance stored in a second chamber, the first and second chambers being located in a nose to tall arrangement in substantial axial alignment with the central longitudinal axis wherein the distal drug cartridge holder assembly has a proximal extremity releasably attach to a distal zone of the proximal drive system, and a distal extremity configured to receive an injection needle; and an axially fixed coupling member operably connecting the piston rod assembly to the drug cartridge holder assembly to impart rotation from the piston rod assembly to the coupling member to collapse the drug cartridge holder assembly in a proximal direction toward the distal tip of the piston rod assembly from the extended configuration along the central longitudinal axis, to the collapsed configuration along the central longitudinal axis to effect reconstitution of an injectable product comprising the at least first and second substances located within only one of said at least first or second chambers after said reconstitution and the piston rod assembly being axially movable in a distal direction relative to and along an axial length of the coupling member to move the distal tip of the piston rod assembly towards the collapsed drug cartridge holder assembly via operation of the drive motor wherein the drug cartridge holder assembly includes a proximal elongated body and a distal elongated body concentrically aligned with the proximal elongated body wherein the proximal and distal elongated bodies each have a bore and the distal elongated body is sized for translation within the bore of the proximal elongated body to collapse the drug cartridge holder assembly from the extended configuration to the collapsed configuration.

2. The handheld motor-driven drug reconstitution and auto-injector device according to claim 1, wherein the coupling member imparts rotation to the proximal elongated body of the drug cartridge holder assembly to move the distal elongated body from the extended configuration to the collapsed configuration.

3. The handheld motor-driven drug reconstitution and auto-injector device according to claim 2, wherein:

the proximal and distal elongated bodies of the drug cartridge holder assembly are connected respectively to one another via contact surfaces comprising an inner surface of the proximal elongated body, and outer surface of the distal elongated body; and when driven by the piston rod assembly of the drive system through the coupling member, the configured permitted movement of the distal elongated body relative to the proximal elongated body of the drug cartridge holder assembly is a rotational movement about the longitudinal axis and along the contact surfaces in the proximal direction to collapse the drug cartridge holder assembly from the extended configuration to the collapsed configuration.

4. The handheld motor-driven drug reconstitution and auto-injector device according to claim 1, wherein the drug cartridge holder assembly comprises:

an outer elongated body releasably connected to a distal zone of the proximal drive system and comprising a bore sized for placement of the proximal and distal elongated bodies in concentric axial alignment with the outer elongated body.

5. The handheld motor-driven drug reconstitution and auto-injector device according to claim 1, wherein the drug cartridge holder assembly further comprises:

an outer elongated body located concentrically around, and over the proximal elongated body and the outer elongated body having a bore in axial alignment with the longitudinal axis and extending in a distal direction from a proximal extremity to a distal extremity;

wherein the distal extremity of the outer elongated body is located concentrically around, and extends over, at least a proximal extremity of the distal elongated body; and when driven by the drive system, the configured permitted movement of the distal elongated body relative to the outer elongated body of the drug cartridge holder assembly is a translational movement along the longitudinal axis in the proximal direction inside the bore of the outer elongated body.

6. A handheld motor-driven drug reconstitution and auto-injector device comprising:

a proximal drive system comprising:

an elongated body having a substantially central longitudinal axis along said elongated body and a bore extending along said longitudinal axis and within said body the elongated body housing a controllable drive motor, and an axially drivable piston rod assembly coupled to said motor located within said bore having a distal tip;

a distal drug cartridge holder assembly having a collapsed configuration and an extended configuration along the central longitudinal axis configured to house a multiple chamber drug cartridge comprising at least a first substance stored in a first chamber and at least a second substance stored in a second chamber, the first and second chambers being located in a nose to tall arrangement in substantial axial alignment with the central longitudinal axis wherein the distal drug cartridge holder assembly has a proximal extremity releasably attach to a distal zone of the proximal drive system, and a distal extremity configured to receive an injection needle;

an axially fixed coupling member operably connecting the piston rod assembly to the drug cartridge holder assembly to impart rotation from the piston rod assembly to the coupling member to collapse the drug cartridge holler assembly in a proximal direction toward the distal tip of the piston rod assembly from the extended configuration along the central longitudinal axis, to the collapsed configuration along the central longitudinal axis to effect reconstitution of an injectable product comprising the at least first and second substances located within only one of said at least first or second chambers after said reconstitution and the piston rod assembly being axially movable in a distal direction relative to and along an axial length of the coupling member to move the distal tip of the piston rod assembly towards the collapsed drug cartridge holder assembly via operation of the drive motor; and a spring biasing member operably coupled to the piston rod assembly and the coupling member to bias the piston rod assembly in the proximal direction relative to the coupling member after injection, or removal of the cartridge holder assembly after reconstitution.

7. A handheld motor-driven drug reconstitution and auto-injector device comprising:

a proximal drive system comprising:

an elongated body having a substantially central longitudinal axis along said elongated body and a bore extending along said longitudinal axis and within said body the elongated body housing a controllable drive motor, and an axially drivable piston rod assembly coupled to said motor located within said bore having a distal tip;

a distal drug cartridge holder assembly having a collapsed configuration and an extended configuration along the central longitudinal axis configured to house a multiple chamber drug cartridge comprising at least a first substance stored in a first chamber, and at least a second substance stored in a second chamber, the first and second chambers being located in a nose to tall arrangement in substantial axial alignment with the central longitudinal axis wherein the distal drug cartridge holder assembly has a proximal extremity releasably attach to a distal zone of the proximal drive system, and a distal extremity configured to receive an injection needle;

an axially fixed coupling member having an elongated length coaxially aligned with the piston rod assembly and operably connecting the piston rod assembly to the drug cartridge holder assembly to impart rotation from the piston rod assembly to the coupling member to collapse the drug cartridge holder assembly in a proximal direction toward the distal tip of the piston rod assembly from the extended configuration along the central longitudinal axis, to the collapsed configuration along the central longitudinal axis to effect reconstitution of an injectable product comprising the at least first and second substances located within only one of said at least first or second chambers after said reconstitution and the piston rod assembly being axially movable in a distal direction relative to and along an axial length of the coupling member to move the distal tip of the piston rod assembly towards the collapsed drug cartridge holder assembly via operation of the drive motor;

at least one projection configured for insertion into at least one elongated longitudinal slot to impart rotation from the piston rod assembly to the coupling member to collapse the drug cartridge holder assembly and the at least one projection being movable along a length of the at least one axial slot between a proximal end and a distal end of the at least one longitudinal slot for translation of the distal tip of piston rod assembly relative to the coupling member in the distal direction towards the collapsed drug cartridge holder assembly; and a biasing member operably coupled to the coupling member and the piston rod assembly to bias the at least one projection towards the proximal end of the at least one longitudinal slot and the at least one projection being moved against the biasing member along the at least one longitudinal slot to move the distal tip of the piston rod assembly in the distal direction towards the collapsed drug cartridge holder assembly.

8. The handheld motor-driven drug reconstitution and auto-injector device of claim 7 wherein the at least one projection is on the piston rod assembly and the at least one longitudinal slot is formed along an outer perimeter of the coupling member.

9. The handheld motor-driven drug reconstitution and auto-injector device of claim 8 wherein the at least one projection includes a plurality of wing projections on the piston rod assembly and the at least one longitudinal slot includes a plurality of longitudinal slots on the coupling member spaced to align with the plurality of wing projections.

10. The handheld motor-driven drug reconstitution and auto-injector device of claim 7 wherein the biasing member is a coil spring disposed between the at least one projection and a distal radially projecting shoulder.

11. The handheld motor-driven drug reconstitution and auto-injector device of claim 7 wherein rotation from the coupling member is imparted to the drug cartridge drug holder assembly via cooperating splines and grooves to collapse the drug cartridge holder assembly from the extended configuration to the collapsed configuration.

12. The handheld motor-driven drug reconstitution and auto-injector device of claim 7 wherein the drug cartridge holder assembly includes a proximal elongated body and a distal elongated body wherein the distal elongated body is sized for translation with a bore of the proximal elongated body and rotation of the drug cartridge holder assembly through the coupling member rotates the proximal elongated body in a first direction and the distal elongated body in a second different direction to translate the distal elongated body within the bore of proximal elongated body to the collapsed configuration and the bore of the proximal elongated body has an annular shoulder to restrict continued rotation of the proximal and distal elongated bodies in the collapsed configuration.

13. The handheld motor-driven drug reconstitution and auto-injector device of claim 12 and comprising an outer elongated body having an inner bore and the proximal and distal elongated bodies are disposed within the inner bore of the outer elongated body and including interlocking features on the outer elongated body and the proximal elongated body to restrict axial movement of the drug cartridge holder assembly in the distal direction.

14. The handheld motor-driven drug reconstitution and auto-injector device of claim 12 and comprising an outer elongated body having an inner bore and the proximal and distal elongated bodies are disposed within the inner bore of the outer elongated body and including features on the outer elongate body to restrict distal axial movement of the distal elongate body in the extended configuration.

15. The handheld motor-driven drug reconstitution and auto-injector device of claim 14 wherein the outer elongated body is threadably connected to the elongated body of the proximal drive system.

16. The handheld motor-driven drug reconstitution and auto-injector device of claim 7 wherein the piston rod assembly includes a piston rod coupled to the drive motor and an elongated internally threaded nut and the at least one projection is formed on the elongated nut and the at least one elongated slot is formed on the coupling member.

* * * * *